United States Patent [19]

Perry et al.

[11] Patent Number: 4,800,892

[45] Date of Patent: Jan. 31, 1989

[54] APPARATUS FOR INFLATING CUFF FOR BLOOD PRESSURE MONITORING SYSTEM

[75] Inventors: William D. Perry; Donald H. Heihn; H. Herbert Peel, all of San Antonio, Tex.

[73] Assignee: Nippon Colin Co., Ltd., Komaki, Japan

[21] Appl. No.: 888,856

[22] Filed: Jul. 21, 1986

[51] Int. Cl.$^4$ ............................................. A61B 5/02
[52] U.S. Cl. ................................... 128/677; 128/682; 128/679; 137/224
[58] Field of Search ...................... 128/672, 677–686; 137/223–224, 225

[56] References Cited

U.S. PATENT DOCUMENTS

| | | | |
|---|---|---|---|
| 2,684,685 | 7/1954 | Learman | 137/225 |
| 3,485,238 | 12/1969 | Kostrov et al. | 128/683 |
| 4,493,326 | 1/1985 | Hill et al. | 128/680 |
| 4,567,899 | 2/1986 | Kamens | 128/680 |
| 4,627,440 | 12/1986 | Ramsey, III et al. | 128/682 |
| 4,660,567 | 4/1987 | Kaneko et al. | 128/682 |

Primary Examiner—Edward M. Coven
Assistant Examiner—Angela D. Sykes
Attorney, Agent, or Firm—Gary W. Hamilton

[57] ABSTRACT

An inflation system for providing rapid, linear inflation of a container, such as an occlusion cuff used in connection with a blood pressure monitoring system. The invention system provides an automatic fast-fill of the cuff to a predetermined pressure level, followed by a smooth, linear pressurization profile which is independent of the volume of the cuff. An efficient electronic actuation system allows the system to inflate the cuff many times using the power supplied by a low power battery. A pressure relief system is provided to automatically terminate operation of the inflation system once systolic pressure has been detected or if the pressure in the system rises above a predetermined level. The system is extremely lightweight and compact, thus allowing a patient to carry the system on his person without undue fatigue.

20 Claims, 7 Drawing Sheets

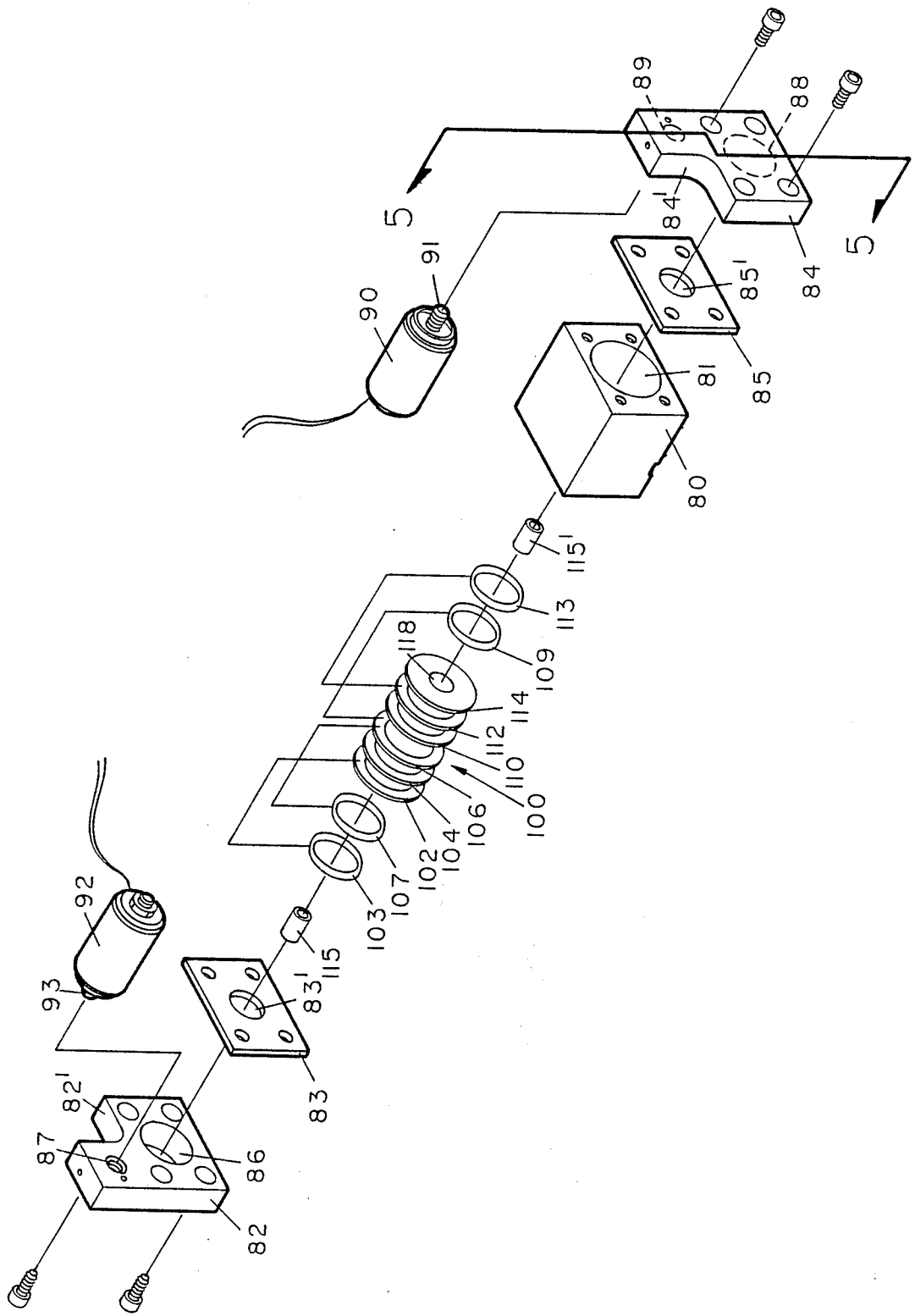

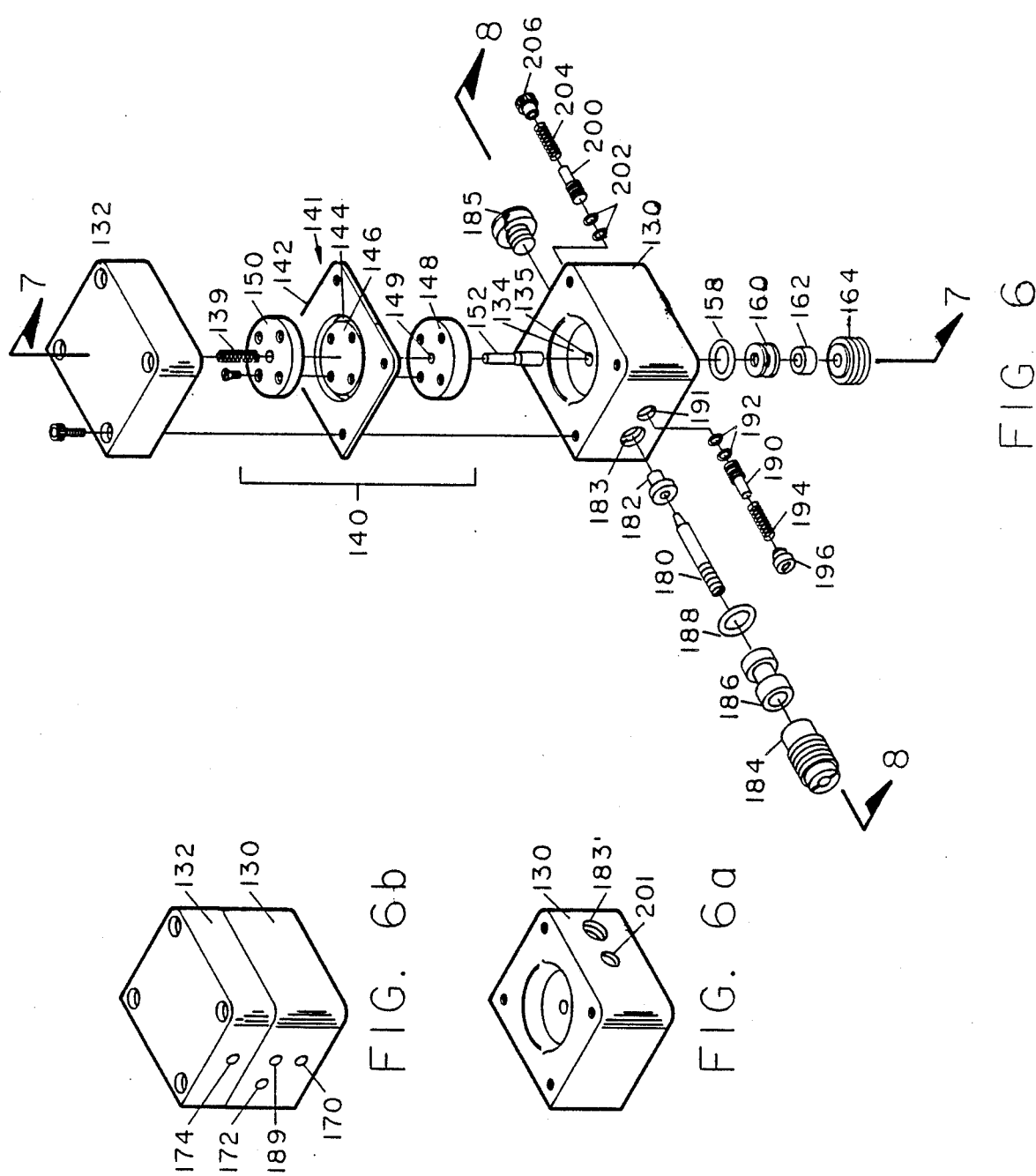

APPARATUS FOR INFLATING CUFF FOR BLOOD PRESSURE MONITORING SYSTEM

FIELD OF THE INVENTION

The present invention relates generally to inflation systems for occlusion cuffs used in connection with blood pressure monitoring systems. In particular, the present invention provides a method and apparatus for automatically controlling the inflation of an occlusion cuff used in monitoring systems for measuring blood pressure.

BACKGROUND

One of the most common systems for obtaining an indirect measurement of a patient's blood pressure is a system which measures pressure variations in a pressurized cuff placed on a patient's arm. Such measurements can be made during either the pressurization or the depressurization of the cuff. The cuff pressurization cycle is commonly referred to as the "upramp," while the depressurization cycle is referred to as the "downramp."

Manual measurements of blood pressure are usually taken on the downramp of the cuff pressurization cycle. In this procedure, an occlusion cuff is rapidly inflated to a pressure level above that at which systolic pressure is expected to occur. Once the maximum pressure has been reached, the pressure in the cuff is slowly decreased while the operator listens for changes in the sound characteristics of the pulse, which changes can be correlated with systolic and diastolic pressure.

Although the cuff inflation system described above can be used to obtain accurate indications of blood pressure, it has a number of drawbacks. In particular, the manual inflation system requires that the cuff be inflated significantly above the expected systolic pressure of the patient. Since the patient's systolic pressure is not known in advance, the cuff is often inflated to an unnecessarily high level which can cause discomfort or even tissue damage to the patient. In addition, the uncertainty over the necessary level of inflation often results in the need to reinflate the cuff several times to obtain an accurate reading of blood pressure.

Automatic blood pressure monitoring systems can be adapted to make blood pressure measurements during either the upramp or the downramp portion of the cuff pressurization curve. It is extremely desirable to have a pressurization or depressurization curve when using an automatic monitoring system. Linearity of the curve significantly decreases the length of time required for the measurement and allows the system to make a more accurate measurement. For systems making measurements on the upramp portion of the cuff pressurization curve, it is also desirable to have the cuff quickly pressurized to a predetermined level, e.g. 40 mm of mercury, to avoid taking unnecessary measurements at pressure levels well below those at which systolic and diastolic pressure are expected to occur.

SUMMARY OF THE INVENTION

The cuff inflation system of the present invention overcomes the difficulties of prior systems by providing an automatic, fast-fill inflation system which rapidly pressurizes to a predetermined pressure level and which then provides a smooth, linear pressurization profile which is independent of the cuff volume. The invention inflation system is a compact, self-contained unit which is lightweight enough to allow the patient to carry the system on his person for extended periods of time without undue stress.

Pressurized gas to inflate the cuff is provided by a small, readily available cylinder of carbon dioxide. An efficient electrical activation system is provided to allow the system to be activated over long periods of time using the power provided by a small, low power battery. A pressure relief system automatically terminates operation of the system once systolic pressure has been detected or if the cuff pressure rises above a level of 300 mm of mercury. Once the inflation cycle has been terminated, the system will automatically reset and deflate the cuff to atmospheric pressure.

BRIEF DESCRIPTION OF THE DRAWINGS

FIG. 4 is an exploded perspective view of the main valve assembly of the invention inflation system showing details relating to the three way spool valve assembly and the electronic actuators.

FIG. 6 is an exploded perspective view of the final regulator assembly.

FIG. 6a is a rear view of the final regulator housing of FIG. 6, showing the arrangement of apertures for receiving valve system components.

FIG. 6b is a left side perspective view of the final regulator housing showing the location of ports for distributing gas streams between the pressure chambers of the regulator.

DETAILED DESCRIPTION OF THE PREFERRED EMBODIMENT

Figure 1:
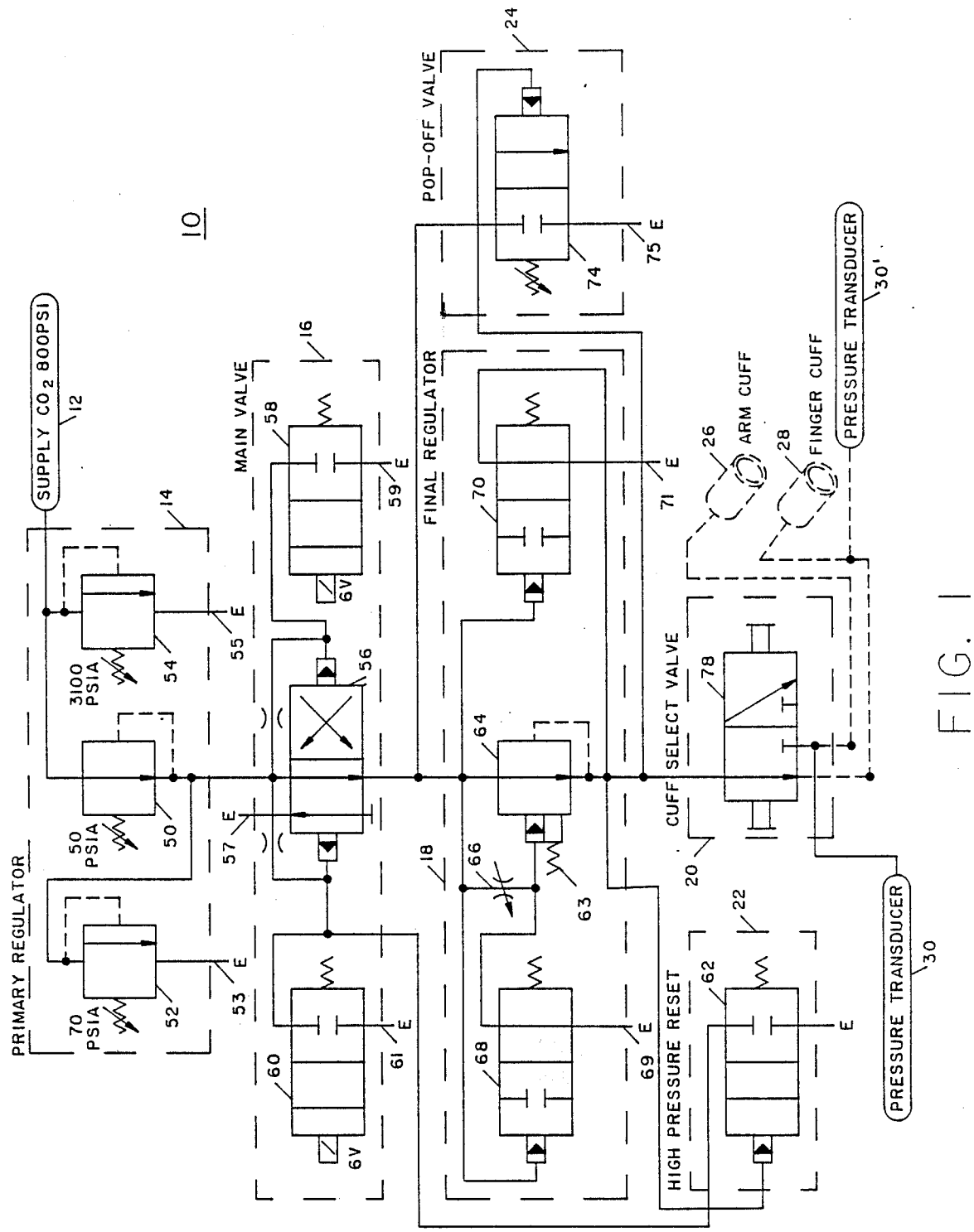
FIG. 1 is a schematic representation of the pneumatic components of the cuff inflation system of the present invention.
Figure 2A:
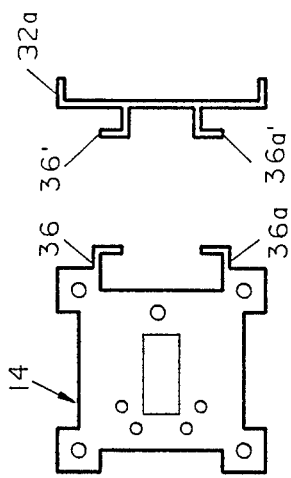
FIG. 2a is a top plan view taken along lines 2—2 of FIG. 2 showing details relating to the sliding interface assembly for mounting the primary regulator assembly on the system manifold.
Figure 2:
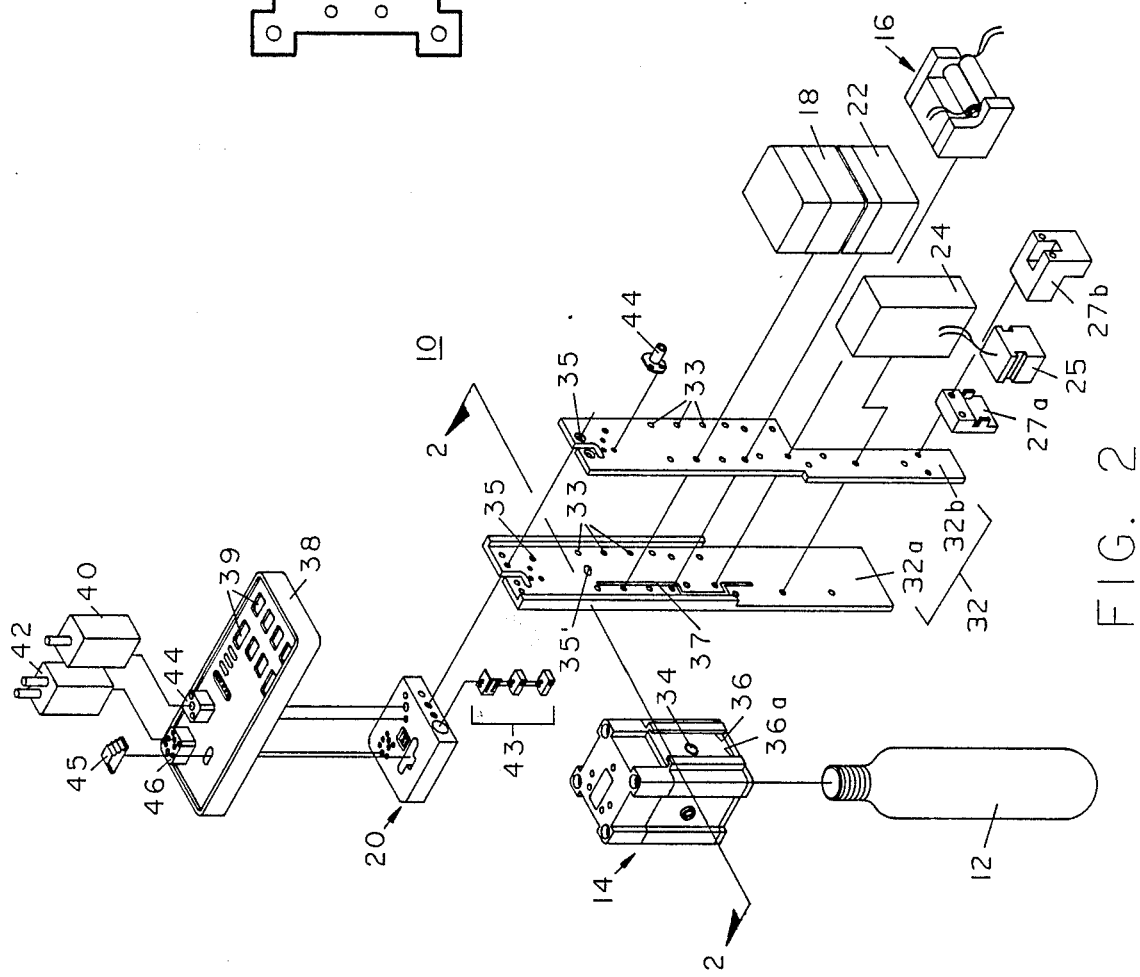
FIG. 2 is an exploded perspective view of the invention cuff inflation system showing the mechanical interrelationship of the major system components.

Referring to the drawings in more detail and to FIGS. 1 and 2 in particular, the cuff inflation system 10 of the present invention is shown in its preferred embodiment. The system uses high pressure gas supplied by a conventional carbon dioxide cylinder 12 to provide a rapid inflation of an occlusion cuff to a predetermined pressure followed by a constant, linear increase in cuff pressure. The system is broadly comprised of six functional modules: the primary regulator assembly 14, the main valve assembly 16, the final regulator assembly 18, the cuff select valve assembly 20, the high pressure reset valve assembly 22 and the pop-off valve assembly 24. The essential operating features of each of these system modules will be described in greater detail below.

The relative size and approximate spatial relation of each of the above-mentioned system components can be seen by referring the exploded perspective view of the preferred embodiment shown in FIG. 2. All of the functional modules are secured to a central manifold assembly 32 comprising manifold plates 32a and 32b. Each of these manifold plates is provided with a plurality of apertures 33 for receiving appropriate mounting hardware to secure the various system modules to the manifold. Additional apertures, illustrated generally by reference number 35, are included in each of the manifold plates to provide ports for the passage of gas between the system modules attached to either side of the manifold 32. Gas is transported along the longitudinal axis of the manifold 32 and distributed to the various modules by a plurality of longitudinal channels, illustrated generally by channel 37 in manifold plate 32a, shown in FIG. 2. Although not explicitly shown in the figures, appropriate gaskets and seals are provided as necessary between all of the system components to provide pneumatic seals.

Figure 3C:
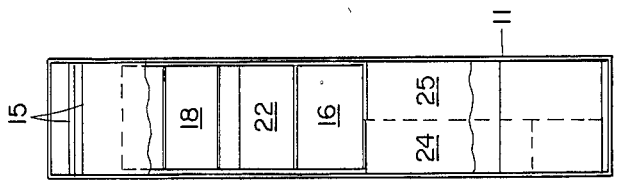
FIG. 3c is a right side plan view of the cuff inflation system taken along section lines 3—3 of FIG. 3a showing the arrangement of the regulator module assemblies and the battery pack within the system case.
Figure 3A:
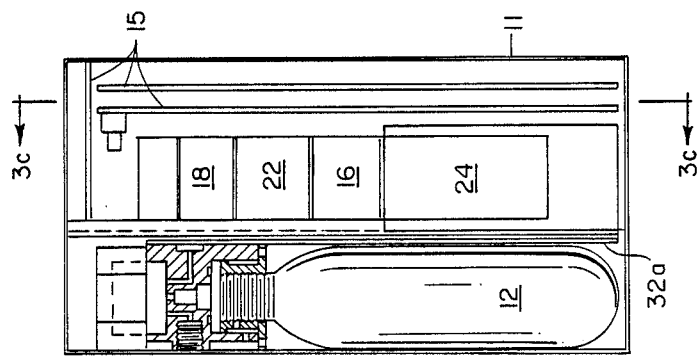
FIG. 3a is a front plan view of the cuff inflation system of the present invention showing the arrangement of the major system components within the system housing.
Figure 3B:
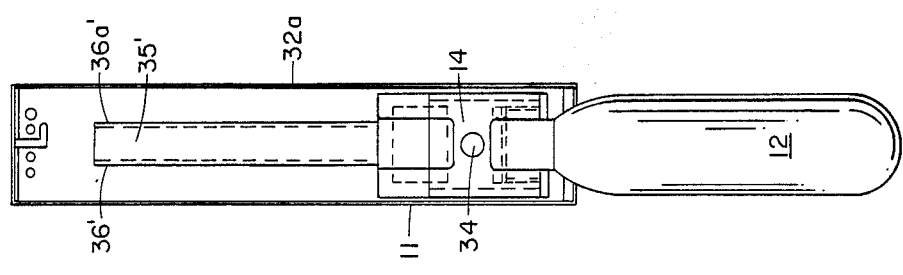
FIG. 3b is a left side plan view of the cuff inflation system showing the carbon dioxide cylinder in the extended position to allow replacement of the cylinder.

A control panel 38, shown in FIG. 2, is attached to the upper portion of the system modules and forms the upper surface of the housing 11 with the system fully assembled, as shown in FIGS. 3a-3c. The control panel contains a plurality of apertures 39 for mounting various electronic controls and contains pneumatic fittings 44 and 46 for receiving complementary pneumatic connectors 40 and 42 for distributing gas to the arm cuff 26 and finger cuff 28, respectively.

The physical arrangement of the various modules of the inflation system 10 when contained within a system housing 11 can be seen by referring to FIGS. 3a-3c. The external dimensions of the system modules are extremely compact, thereby allowing the pneumatic components and electronic control circuit boards 15 to be enclosed in a housing having a width of 3.50 inches, a height of 6.75 inches and a thickness of 1.40 inches.

One of the important novel features of the invention cuff inflation system is the sliding pneumatic interface between the primary regulator 14 and the system manifold 32. As can be seen in FIG. 2, one face of the primary regulator assembly 14 is provided with a pair of spaced guide rails 36 and 36a having inwardly directed outer surfaces. The guide rails 36 and 36a of the primary regulator 14 are received in slidable relation with complementary rails 36' and 36a', shown in FIG. 2a, on the outer opposing face of manifold plate 32a. This interlocking guide rail configuration allows the primary regulator assembly 14 to slide in a vertical direction along the vertical longitudinal axis of the system manifold plate.

With the primary regulator assembly 14 in the uppermost vertical position, as shown in FIG. 3a, the carbon dioxide cartridge 12 is completely contained within the housing 11. With the cartridge 12 in this position, the aperture 34 in the primary regulator assembly 14 is aligned with a complementary aperture 35' in the manifold plate 32a, shown in FIG. 2, thus allowing the regulated gas stream provided by the carbon dioxide cylinder 12, via the primary regulator 14, to enter the manifold 32 and be distributed to the system modules.

To remove the cartridge 12 from the system, the primary regulator assembly 14 is moved downwardly to the position shown in FIG. 3b. In this position, the aperture 34 in the primary regulator assembly 14 is offset from the aperture 35' in the manifold plate 32a and is sealed by contact with the opposing face of the manifold plate 32a. With the cartridge 12 protruding below the lower edge of the housing 11, the cartridge can easily be removed by hand. A new cartridge can be installed in the system by engaging the upper threaded collar of the cartridge with complementary threads in the annular mounting ring of the lower portion of the primary regulator. As the cylinder is screwed into the primary regulator 14, the seal on the cylinder is penetrated thus allowing the gas to flow into the module.

The sliding interface between the primary regulator assembly and the manifold offers numerous advantages in terms of compactness and reduction in the number of components. The ability to slide the primary regulator assembly 14 to remove the cartridge 12 simplifies the housing design and allows the external dimensions of the unit to be kept to a minimum. Also, the sliding interface provides a means for allowing the primary regulator to move within the system housing without cumbersome loops of pneumatic tubing. Further, the seal between the aperture 34 of the primary regulator and the opposing face of the manifold plate 32a obviates the need for a system of valves to seal the system during replacement of the cartridge 12.

The functional characteristics of each of the system modules can be seen by referring again to FIG. 1. The gas supplied by the carbon dioxide cylinder 12 initially enters the primary regulator module 14 at a pressure of 800 pounds per square inch (psi). The pressure of the gas stream is reduced to 50 psi by pressure regulator 50 and is then distributed to the main valve assembly 16 via the system manifold. The primary regulator 14 also contains two pressure relief valves to correct abnormal pressure conditions on either the high pressure side or low pressure side of the regulator 50. A high pressure relief valve 54 is connected to the high pressure side of the pressure regulator 50 to control the raw pressure of the gas stream provided by the carbon dioxide cylinder 12. This valve is incorporated as a safety feature to relieve excess pressure in the primary regulator. Excess gas is vented from the pressure relief valve 54 via exhaust vent 55. The pressure relief valve 54 used in the preferred embodiment is designed to relieve pressure above 3100 psi. This is approximately the pressure in a typical carbon dioxide cylinder exposed to an ambient temperature of 160° F., and is well below the 6000 psi proof test limit of the cylinder.

The second pressure relief valve 52 is connected to the low pressure side of the regulator 54. This relief valve is adjustable, but in the preferred embodiment it is normally set to relieve pressures above 70 psi, which is above the normal operating pressure. Excess gas is vented from the pressure relief valve 52 via exhaust vent 53.

The 50 psi regulated gas stream from the primary regulator 14 is routed through the system manifold to the main valve assembly 16. The main valve assembly 16 comprises a double-piloted, three-way spool valve shown schematically by reference number 56. The pilots 58 and 60 for the spool valve 56 are electrically actuated requiring a 6-volt signal for a maximum of 2 seconds to actuate the spool valve 56 and cause it to change position. Once the spool valve 56 has changed position, no additional electric current is required, and the valve will stay in its new position until the other pilot valve is actuated thus causing the spool valve to change position. The mechanical components which are used to achieve the functional characteristics of the main valve assembly will be discussed in greater detail below.

When an electronic control signal to start the inflation cycle is sent to the main valve, the spool moves to the "ON" position and allows a 50 psi stream of carbon dioxide gas to flow through the system manifold to the input of the final regulator 18. The spool valve 56 will remain in the open position until a control signal is sent to the main valve module to terminate the inflation cycle, or until the output pressure of the final regulator 18 reaches 300 mm of mercury, thereby causing the high pressure reset valve assembly 22 to terminate the inflation cycle as discussed below.

An auxiliary pilot port which allows the spool valve 56 to be turned off is also included in the main valve module 14. This auxiliary pilot port is actuated by the high pressure reset assembly 22. The high pressure reset assembly comprises a piloted relief valve 62 which opens when the output pressure of the final regulator 18 reaches a pressure of 300 mm of mercury. When the valve opens, pressure from the auxiliary port on the piloted main valve assembly 16 is exhausted via exhaust port 61 and the main valve is turned to the "OFF" position, thus terminating the flow of gas to the final regulator assembly 18. The automatic shutdown feature of the high pressure reset valve assembly 22 is entirely independent of the electric power in the system and will function even if the control system or batteries should fail.

The final regulator assembly 18 comprises a pressure-piloted pressure regulator 64 having its output controlled by pilots 68 and 70. A spring assembly, illustrated schematically by reference number 63, provides the initial set point of 40 mm of mercury for system pressurization. Thus, when pressure is applied to the input port of the assembly, the regulator immediately sets the output pressure at 40 mm of mercury. The flow from the regulator 64 will be maximum until this pressure has been reached. The cooperation between the spring and the other mechanical components of the final regulator assembly to achieve the desired initial cuff pressurization is discussed further below.

An adjustable control orifice 66 bleeds pressure from the input at 50 psi into the pilot 68 of the pressure regulator 64. Based on the size of the adjustable control orifice 66 and the volume of the pilot, a linear increase in pilot pressure is produced starting at 40 mm of mercury and increasing with time. Since the size of the orifice 66 and the volume of the pilot 68 are fixed values, the rate of increase in pressure is independent of the volume of the cuff attached to the output of the final regulator assembly 18. As the pressure in the pilot 68 of the regulator 64 increases, the regulator forces the pressure at the output to match the pilot pressure thereby maintaining a linear increase in the cuff pressure.

The output of the final regulator assembly 18 is routed to the cuff select valve assembly 20 and also to the high pressure reset assembly 22, as discussed above. The cuff select valve allows the inflation system to have two cuffs attached to the gas stream, with the ability to switch quickly between the cuffs. The cuff select assembly comprises a manually operated spool valve 78 which routes the output of the inflation system to either of the pneumatic cuff connectors 40 or 42, shown in FIG. 1. When the valve is in the position to select the arm cuff, the pressure is routed simultaneously to the arm cuff and to the pressure transducer 30. When the valve is in the finger cuff position, the pressure is routed to the finger cuff and the port to the arm cuff pressure transducer 30 is blocked so that the pressure is measured in a pressure transducer 30' which is built into the finger cuff. The cuff select valve is also connected to a microswitch assembly 43, shown in FIG. 2, which indicates to the electronic control system whether the arm cuff or the finger cuff has been selected to ensure that the proper algorithms are used to evaluate the output of the respective transducer.

One of the safety features of the invention cuff inflation system is a cuff pressure pop-off valve assembly 24 which ensures that the pressure in the cuff cannot exceed 320 mm of mercury. As was discussed above, the invention system is designed to inflate the cuff until systolic pressure is detected at which point the electronic control system resets the inflation system and the cuff is deflated. If the system should fail to reset or if the batteries should fail, the high pressure reset valve assembly 22 turns the system off and deflates the cuff when the pressure reaches 300 mm of mercury. The cuff pressure pop-off valve serves as an additional layer of protection in the event that the high pressure reset valve assembly 22 should fail to function when the cuff pressure exceeds 300 mm of mercury.

The cuff pressure pop-off valve of the preferred embodiment comprises a pressure piloted latching two-way valve which actuates if the pressure in the cuff exceeds 320 mm of mercury. At that pressure level, the valve opens and dumps the excess carbon dioxide gas into the atmosphere. Once the valve has been actuated, it remains in the open position until the supply of carbon dioxide has been completely exhausted.

Figure 5A:
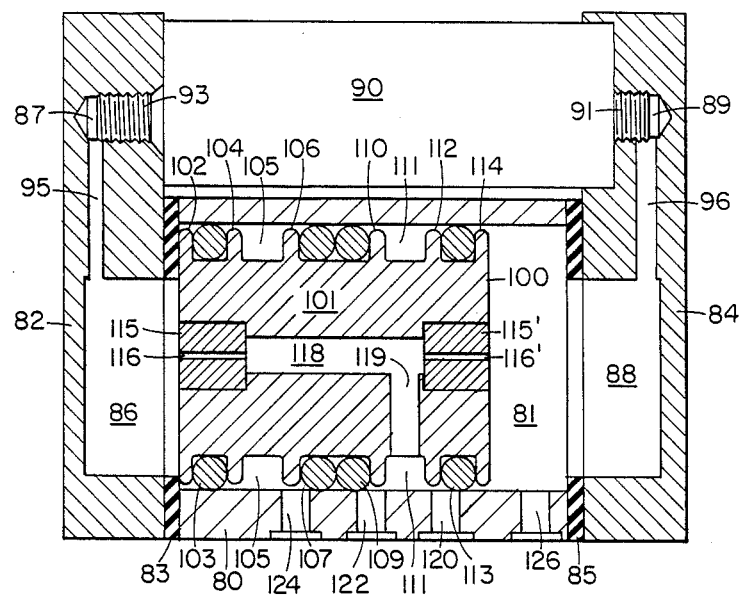
FIG. 5a is a cross sectional view of the main valve assembly showing details relating to the distribution of gas streams with the three way spool valve in the "OPEN" position.
Figure 5B:
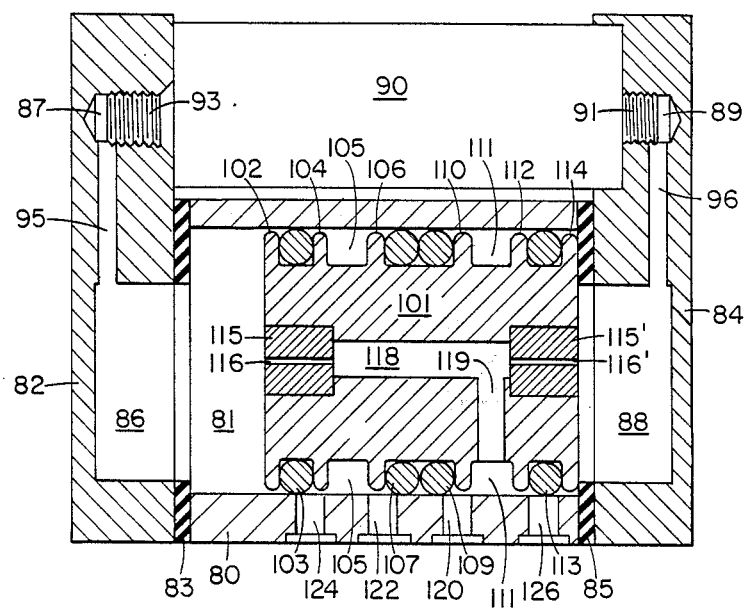
FIG. 5b is a cross sectional view of the main valve assembly showing details relating to the distribution of gas streams with the three way spool valve in the "CLOSED" position.

Details relating to the main valve assembly 16 can be seen by referring to the exploded diagram of the assembly, shown in FIG. 4, and to the cross sectional diagrams shown in FIGS. 5a and 5b. The central valve body 80 consists of an elongated cube having a centrally disposed longitudinal bore 81. The lower face of the valve body 80 contains a plurality of apertures, shown in FIGS. 5a and 5b, for communicating streams of gas into and out of the valve assembly. The role of these apertures in the operation of the main valve assembly will be discussed in greater detail below. The ends of the longitudinal bore 81 are closed by securing end caps 82 and 84 to the central valve body 80 with rubber gaskets 83 and 85 providing a pneumatic seal between the respective components of the housing. In addition to providing a pneumatic seal, these rubber gaskets provide a cushion for the valve spool as it moves between the open position shown in FIG. 5a and the closed position shown in FIG. 5b.

As can be seen in FIG. 4, the left end cap 82 has a cylindrical depression 86 in its inner face. In the assembled valve module, shown in cross-section in FIGS. 5a and 5b, this depression 86 forms a pressure chamber which serves as one of the pressure pilots for moving the valve spool within the assembly. A similar depression 88, shown in phantom in FIG. 4, forms a pressure chamber which serves as a pilot for the opposite side of the valve assembly. The pressure chamber 86, shown in FIGS. 5a and 5b corresponds to the pilot 58 shown schematically in the main valve module of FIG. 1. Likewise, the pressure chamber 88 corresponds to the schematic pilot 60 of FIG. 1. As can be seen in FIGS. 5a and 5b, the respective pilots are actually formed by the combination of a portion of the longitudinal bore 81 of the valve body 80 and the chambers 86 and 88. For purposes of discussion, however, these pressure chambers will be referred to as pressure chamber 86 or 88.

Two electronic solenoid exhaust valve actuators 90 and 92 are attached to the top of the main valve assembly to actuate the main valve pilots in a manner described below. As can be seen in FIG. 4, actuator 92 has a threaded pneumatic connector 93 which is received in a threaded aperture 87 in the upper portion of endcap 82. The aperture 87 is connected to the pressure chamber formed by the cylindrical depression 86 via an internal channel 95 in the interior of endcap 82, as can be seen in FIGS. 5a and 5b. The threaded connector on actuator 91 is similarly received in threaded aperture 89, shown in phantom in FIG. 4, in endcap 84. The aperture 89 is connected to the chamber formed by cylindrical depression 88 by an internal channel 96 in endcap 84.

As can be seen in FIG. 4, each of the end caps 82 and 84 has a scallop, 82' and 84', respectively, in one upper corner to allow the actuator connected to the opposite end cap to be received in a very close-fitting relationship. The actuators of the preferred embodiment are attached to the assembly in a side-by-side mounting arrangement which allows the size of the module to be kept to a minimum.

The valve spool assembly 100 comprises a generally tubular central body core 101 with a plurality of transverse annular rings 102, 104, 106, 110, 112, and 114 in a spaced relation along the longitudinal axis of the body core 101. The diameter of the annular rings is slightly smaller than the diameter of the circular bore 81 of the central body 80 so that the spool assembly 100 can be slidably received therein. Four O-rings are received between selected pairs of the annular rings to define a system of pneumatic seals and passages which control the flow of gas streams within the valve assembly. As can be seen in FIGS. 5a and 5b, O-ring 103 is attached to the spool assembly in the depression between annular rings 102 and 104 to define a seal along the left outer circumferential edge of the spool assembly 100. Two O-rings, 107 and 109, are attached between annular rings 106 and 110 to provide a seal along the central portion of the spool. Finally, O-ring 113 is attached to the spool between annular rings 112 and 114 to provide a seal along the right outer circumferential edge of the spool.

As can be seen in FIGS. 5a and 5b, there is no O-ring between the annular rings 104 and 106. The space between these rings defines an annular pressure chamber 105 which is sealed by the O-rings 103 and 107 on either side of the chamber. Similarly, the space between the rings 110 and 112 defines an annular pressure chamber 111 which is sealed by O-rings 109 and 113. These annular pressure chambers cooperate with the apertures in the lower face of the valve body 80 to distribute gas streams through the valve assembly in a manner described below.

Referring again to FIGS. 5a and 5b, it can be seen that gas is distributed through the central body core 101 of the valve spool 100 via an internal channel comprising a central longitudinal bore 118 and transverse bore 119. Gas flowing through the longitudinal bore 118 is distributed to the chambers on either side of the spool through the apertures 116 and 116' of orifice fittings 115 and 115', respectively.

As was mentioned above, the lower face of the main valve body 80 contains a plurality of apertures for directing gas streams to and from the main valve assembly. Aperture 120 is connected to the output of the primary regulator module 14 and provides a 50 psi regulated gas stream into the main valve assembly. Aperture 122 is connected to the final regulator assembly; aperture 124 is the main valve exhaust; and aperture 126 is connected to the high pressure reset valve assembly 22.

With the spool 100 in the "OFF" position shown in FIG. 5b, the 50 psi gas stream from the primary regulator passes into the interior of the spool assembly through the path defined by aperture 120, annular pressure chamber 111 and internal channels 119 and 118. The gas stream then passes through the apertures 116 and 116' in orifice fittings 115 and 115', respectively, to pressurize the chambers on either side of the spool assembly 100. With the spool in this position, the chamber 88 on the right side of the spool will be at 50 psi, as will the chamber 86 on the left side of the spool. Since the spool has a pressure of 50 psi on both sides, it is in a balanced condition and does not move.

With the valve in the "OFF" position, the O-rings 107 and 109 provide a seal preventing the flow of 50 psi gas from aperture 120 to aperture 122, which is connected to the final regulator. Instead, the aperture 122 is connected via annular chamber 105 to the exhaust aperture 124.

To initiate the inflation cycle, the electronic solenoid valve 92 is activated for a very short time interval to allow gas to be exhausted from pressure chamber 86 via channel 95. Since the gas is flowing into the chamber at a much slower rate than it is being exhausted, the pressure in this chamber drops very rapidly, thus creating a force imbalance on the spool 100. The higher pressure in the chamber 88 causes the spool 100 to move rapidly to the left, thereby changing the main valve to be in the "ON" position shown in FIG. 5a.

With the valve spool 100 in the "ON" position shown in FIG. 5a, the 50 psi regulated gas stream from aperture 120 passes to the final regulator via the path defined by annular chamber 111 and aperture 122. The 50 psi also continues to flow into the interior of the valve spool 100 to repressurize each of the pilot chambers 86 and 88 to 50 psi to recreate the balanced force condition.

With the valve spool in the "ON" condition shown in FIG. 5a, the main valve can be turned off either electronically, by actuating the solenoid valve 90, or by action of the reset valve assembly 22. Electronic actuation of the solenoid valve 90 will cause the gas in the pilot chamber 88 to be exhausted via channel 96, thus causing a pressure imbalance which will move the valve spool to the right into the "OFF" position. Similarly, if the gas in the pilot 86 is exhausted through the reset valve via aperture 126, a pressure imbalance will be created which will move the valve spool 100 to the "OFF" position.

As was discussed above, the regulated 50 psi gas stream is routed by the system manifold from the main valve assembly 16 to the final regulator 18. The final regulator is designed to provide a linear increase in pressure regardless of the volume of the cuff. A regulator system for providing a linear increase in cuff pressure is shown generally in U.S. Pat. No. 4,587,974, issued to Link, which by this reference is incorporated for all purposes. The regulator system shown in said patent comprises a housing defining adjacent internal active and control pressure chambers which are separated from one another in an air sealed manner by a diaphragm. The two pressure chambers are connected by a tubular assembly having a constricted passageway, which creates a very small pressure differential between the two chambers when the system is pressurized. A valve system cooperating with the diaphragm regulates the flow of gas into the respective chambers in response to movement of the diaphragm. The two pressure chambers are maintained at essentially equal pressures, except for a very small pressure differential related to the drop across the constricted tubular connection between the chambers. Because the two chambers are maintained at approximately equal pressures, the pressurization of the cuff attached to the active chamber is assumed to increase linearly independent of cuff volume.

The final regulator of the invention provides an alternate and improved system over that shown in the above-mentioned patent for providing a linear increase in cuff pressure independent of cuff volume. The invention final regulator system provides a tracking regulator controlled by a choked flow orifice yielding a constant mass flow rate. The pressure chambers in the invention regulator system, as described below, are maintained at a significant pressure differential. The magnitude of this pressure differential is related to a means for providing an initial pressurization level of the cuff. The invention system allows the cuff to be quickly pressurized to a predetermined level and then to be pressurized linearly independent of the volume of the cuff. The initial pressurization of the cuff significantly reduces the amount of time required to make a measurement of the patient's blood pressure.

Figure 7:
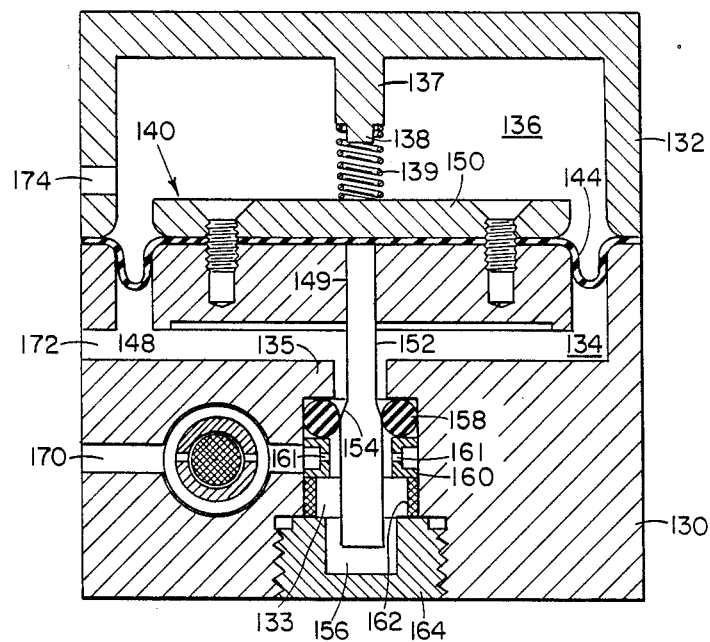
FIG. 7 is a cross sectional view of the final regulator assembly taken along lines 7—7 of FIG. 6, showing details relating to the valve piston assembly and the pressure chambers.
Figure 8:
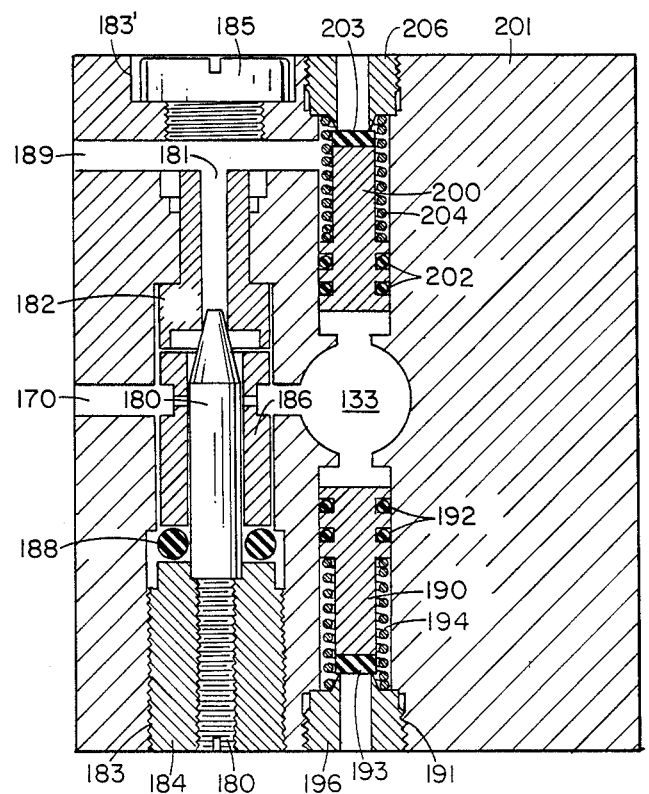
FIG. 8 is a cross sectional view taken along lines 8—8 of FIG. 6 showing details relating to the adjustable orifice and the exhaust valve assemblies.

Details relating to the preferred embodiment of the final regulator valve assembly 18 can be seen by referring to FIGS. 6 through 8. The regulator housing comprises a lower main body 130 and an upper main body 132. The lower main body 130 includes a cylindrical depression 134, which defines a pressure chamber, which can be seen best in FIG. 7. Similarly, the interior of the upper body housing 132 defines a pressure chamber 136 when attached to the lower main body 130. A shaft 137 having a lower portion 138 of reduced diameter protrudes downwardly from the center of the inner surface of the upper body housing 132 and supports a spring 139 which exerts a force on the piston assembly 140 to provide a setting for initial system pressurization, as described in greater detail below.

The piston assembly 140 comprises a diaphragm assembly 141, a lower piston body 148 and an upper piston cap 150. The diaphragm assembly 141 includes a rectangular mounting surface 142, a flexible annular rim 144 and a circular center portion 146. The circular center portion 146 is sandwiched between the lower piston body 148 and the upper piston cap 150 to form an integral piston assembly as shown in the cross sectional view of FIG. 7. The piston assembly 140 is secured in the regulator housing by the mounting surface 142 which is attached between upper and lower housing members 103 and 132, respectively. A tapered piston rod 152 is secured in aperture 140 of the lower piston body 148 and extends downward through aperture 135 in lower housing body member 130. The tapered piston rod 152 has an enlarged base portion 156 which is supported in chamber 133 of lower main body 130 by a mounting assembly comprising an O-ring 158, an annular collar 160, a tubular spacer 162 and threaded cap 164. The annular collar 160 contains a plurality of apertures 161 for allowing passage of a regulated stream of 50 psi gas from input port 170 to the interior of chamber 133. Gas from chamber 133 can be communicated upward through the passage between the piston rod 152 and O-ring 158 to the lower pressure chamber 134 and to the cuff via port 172.

The adjustable control orifice, shown schematically by reference number 66 in FIG. 1, consists of a needle valve assembly shown in FIGS. 7 and 8. The needle valve assembly comprises a threaded needle valve 180 and a needle valve seat 182 which are received in a bore 183 in the main body 130 of the final regulator. The needle valve assembly is secured within the regulator body by a threaded mounting plug 184 and an O-ring spacer 186 having an O-ring 188 mounted thereon to provide a pneumatic seal.

As can be seen in FIG. 8, the mounting plug 184 has a threaded inner bore which allows adjustment of the position of the needle valve 180 with respect to the valve seat 182 to control the rate of flow of gas into the inner channel 181 of the valve seat 182. Gas passing through the channel 181 is directed out of port 189 and to the input orifice 174 of the upper pressure chamber 136 of the regulator to provide pilot pressure to maintain linear inflation of the cuff as will be discussed below.

The final regulator body 130, shown in FIG. 7, also houses exhaust valve assemblies corresponding to the exhaust valves shown schematically in FIG. 1. The exhaust valve corresponding to schematic exhaust valve 70 comprises a valve piston 190 having two O-rings mounted thereon, a spring 194 and a threaded connector 196. Similarly, the schematic exhaust valve 68 of FIG. 1 comprises valve piston 200 having two O-rings 202 mounted thereon, a spring 204 and a threaded connector 206. The arrangement of each of these exhaust valve assemblies within the regulator housing 130 can be seen by referring to FIGS. 6 and 8.

Operation of the final regulator can be seen by referring again to FIGS. 7 and 8. In the absence of any pressurized gas stream from input port 170, the spring 130 will exert a downward force on the piston assembly 140, thereby causing the piston rod 152 to move downward and allow passage of gas between the tapered portion 154 of the rod and the O-ring 158. To begin pressurization of the final regulator, a regulated stream of 50 psi gas is provided by main valve assembly 16 to the input port 170 of the final regulator assembly. The 50 psi gas is passed through the apertures 161 in collar 160 to chamber 133 and upward past the O-ring 158 into the lower pressure chamber 134. As the gas pressurizes the lower pressure chamber 134, the piston assembly 140 rises, thus offsetting the force of the spring 139 and allowing a stream of gas is passed to the cuff via port 172. In the preferred embodiment, the spring 139 which exerts downward pressure on the piston assembly is chosen to have a spring constant which gives a rapid initial pressurization to 40 mm of mercury in the lower chamber 134. This rapid rise in cuff pressure offers the advantage of significantly reducing the amount of time required to measure the patient's blood pressure.

The 50 psi gas supplied by the input port 172 is also routed to the adjustable needle valve assembly, as shown in FIG. 8. This stream of gas is directed past the needle valve 180 and to the system manifold via port 189. The system manifold directs this stream of gas through pilot input port 174 and into upper pressure chamber 136, shown in FIG. 7. Because the gas stream passed through port 174 is contained in a constant volume, there is a linear rise in pressure in the upper pressure chamber 136. The pressurization characteristics of the upper chamber are controlled by the needle valve which can be adjusted to change the rate of increase in pressurization of the chamber.

As can be seen from the above discussion there will always be a balanced differential pressure condition between the upper and lower pressure chambers 136 and 134, respectively. Since the output port directing gas to the cuff is connected to the lower chamber 134, the linear rise in pressure in the lower chamber will be translated into a linear increase in the gas pressure in the cuff. Furthermore, the time rate of change of cuff pressure is independent of cuff volume with the flow range of the regulated gas stream.

The invention cuff inflation system offers numerous advantages over prior cuff inflation systems. It is extremely compact and lightweight so that an ambulatory patient can carry the system on his person for long periods of time. The system requires only a short pulse of electric current to turn the system "ON" and another short pulse to turn the system "OFF." This allows the system to be operated for a long period of time using only the current provided by a small battery pack. The gas pressure for the system is provided by a commercially available high-pressure carbon dioxide cylinder. Because of the efficiency of the main valve assembly, such a cylinder contains sufficient gas to allow the cuff to be pressurized for 80 to 100 typical cuff inflations.

The invention cuff inflation system also provides a number of safety features to protect the patient. As was mentioned above, the system normally terminates the inflation cycle when systolic pressure is detected. As a safety precaution, the system automatically turns off if the pressure reaches a value of 300 mm of mercury. This automatic shutdown is independent of electric power in the system and will function even if the control system or batteries should fail. An additional barrier to overpressurization is provided by the pop-off valve assembly which terminates operation of the system when the pressure at the output of the final regulator should reach 320 mm of mercury. This additional safety system ensures that the inflation cycle will be terminated in the event that both the electronic control system and the high pressure reset valve should fail to operate properly.

While the invention method and apparatus for inflating a cuff for use in a blood pressure monitoring system has been described in connection with the preferred embodiment, it is not intended to limit the invention to the specific form set forth herein, but on the contrary, it is intended to cover such alternatives, modifications and equivalents as may included within the scope of the invention as defined by the appended claims.

We claim:
1. An inflation system, comprising:
a pressurizable container;
means for supplying a first gas stream at a first pressure;
first regulator means having an input port and an output port, said input port receiving said first gas stream at said first pressure, said regulator comprising first means for converting said first gas stream at said first pressure to a regulated second gas stream at a second pressure, said second gas stream being communicated from said first regulator means through said output port;
first valve means for controlling the flow of said second gas stream from said output port of said first regulator means; and
second regulator means having an input port for receiving said second gas stream from said output port of said first valve means and having an output port in airflow communication with said pressurizable container, said second regulator means comprising means for converting said second gas stream at said second pressure to a third regulated gas stream having a pressure which increases linearly with time, said third gas stream pressurizing said container in a substantially linear manner independent of the volume of said container.

2. An inflation system according to claim 1, further comprising first pressure relief means in air flow communication with said input port of said first regulator means and second pressure relief means in air flow communication with said output port of said first regulator means, said first pressure relief means operable to interrupt the flow of said first gas stream to said input port if the pressure of said first gas stream is in excess of a first predetermined level, said second pressure relief means operable to interrupt the flow of said second gas stream from said output port if the pressure of said second gas stream is in excess of a second predetermined level.

3. An inflation system according to claim 2 said first pressure relief means operable to interrupt the flow of said first gas stream to said first regulator means if the pressure of said first gas stream is in excess of 3100 pounds per square inch, said second pressure relief means operable to interrupt the flow of gas from said output port of said first regulator means if the pressure of said second gas stream is in excess of 70 pounds per square inch.

4. An inflation system according to claim 3, said first valve means comprising an electronically actuated, piloted valve assembly.

5. An inflation system according to claim 4, said valve assembly comprising: a valve housing having an internal cavity; a valve member slidably received in said cavity and being movable therein between a first position and a second position, said valve member defining a path for said second gas stream in said first position and blocking the flow of said second gas stream in said second position; first and second pressure chamber means for controlling the position of said valve member within said housing; and first and second electronically actuated solenoid exhaust valve means for changing the pressure in said first and second pressure chamber means to cause said valve element to move from said first position to said second position.

6. An inflation system according to claim 5, said second regulator means comprising a tracking regulator having a constant mass flow rate, said tracking regulator comprising an adjustable, choked flow orifice for controlling the rate of increase in pressure of said third regulated gas stream.

7. An inflation system according to claim 6, said second regulator means further comprising control means for maximizing the flow from said output port of said second regulator means until said container has been pressurized to a predetermined initial pressure.

8. An inflation system according to claim 7, said predetermined initial level of pressure in said container being 40 mm of mercury.

9. An inflation system according to claim 7, said second regulator means comprising: a valve housing having first and second cavities therein; a piston received in said housing; a diaphragm attached to said piston and said housing to define a pneumatic seal between said first and second cavities, said piston and diaphragm being movable in said housing in responses to changes in pressure in said first and second cavities; means for placing said first and second cavities in airflow communication with one another; means for placing said second cavity in airflow communication with said container; valve means cooperating with said piston to control the flow of said second gas stream into said second regulator means, said valve means permitting said second gas stream to enter said first and second cavities when the pressure in said first cavity is greater than the pressure in said second cavity by an amount slightly greater than said predetermined initial pressure of said container.

10. An inflation system according to claim 9, further comprising third pressure relief means in air flow communication with said third gas stream, said third pressure relief means operable to interrupt the flow of gas into said second regulator means if the pressure of said third gas stream is in excess of a predetermined level.

11. An inflation system according to claim 10, said predetermined pressure level of said third gas stream being equal to approximately 300 mm of mercury.

12. An inflation system, comprising:
a pressurizable container;
means for supplying a first gas stream at a first pressure;
means defining a system manifold, said manifold comprising a plurality of apertures for distributing streams of gas into and out of said manifold, said manifold further comprising a plurality of internal channels for distributing streams of gas within said manifold;
first regulator means having an input port and an output port, said input port receiving said first gas stream at said first pressure, said regulator comprising first means for converting said first gas stream at said first pressure to a regulated second gas stream at a second pressure, said second gas stream being communicated from said first regulator means through said output port into a complementary input port in said system manifold;
first valve means for controlling the flow of said second gas stream from said output port of said first regulator means into said system manifold;
second regulator means receiving said second gas stream from said system manifold, said second regulator means comprising means for converting said second gas stream at said second pressure to a third gas stream having a pressure which is variable with time, said third gas stream increasing with time to cause said container to pressurize in a substantially linear manner independent of said predetermined volume of said container.

13. An inflation system according to claim 12, said manifold further comprising a mounting means for slidably mounting said first regulator means thereon, said first regulator being slidable between a first position wherein said output port of said first regulator is aligned with said complementary input port of said manifold to allow the communication of said second gas stream into said manifold and a second position wherein said output port is offset from said complementary input port to define a pneumatic seal between said output port and said complementary input port.

14. An inflation system according to claim 13, further comprising first pressure relief means in air flow communication with said input port of said first regulator means and second pressure relief means in air flow communication with said output port of said first regulator means, said first pressure relief means operable to interrupt the flow of said first gas stream to said input port if the pressure of said first gas stream is in excess of a first predetermined level, said second pressure relief means operable to interrupt the flow of said second gas stream from said output port if the pressure of said second gas stream is in excess of a second predetermined level.

15. An inflation system according to claim 14, said first valve means comprising: a valve housing having an internal cavity; a valve member slidably received in said cavity and being movable therein between a first position and a second position, said valve member defining a path for said second gas stream in said first position and blocking the flow of said second gas stream in said second position; first and second pressure chamber means for controlling the position of said valve member within said housing; and first and second electronically actuated solenoid exhaust valve means for changing the pressure in said first and second pressure chamber means to cause said valve element to move from said first position to said second position.

16. An inflation system according to claim 15, said second regulator means comprising a tracking regulator having a constant mass flow rate, said tracking regulator comprising an adjustable, choked flow orifice for controlling the rate of increase in pressure of said third regulated gas stream.

17. An inflation system according to claim 16, said second regulator means further comprising control means for maximizing the flow from said output port of said second regulator means until said container has been pressurized to a predetermined initial pressure.

18. An inflation system according to claim 17, said predetermined initial level of pressure in said container being 40 mm of mercury.

19. An inflation system according to claim 18, said second regulator means comprising: a valve housing having first and second cavities therein; a piston received in said housing; a diaphragm attached to said piston and said housing to define a pneumatic seal between said first and second cavities, said piston and diaphragm being movable in said housing in response to changes in pressure in said first and second cavities; means for placing said first and second cavities in airflow communication with one another; valve means cooperating with said piston to control the flow of air into said second regulator means, said valve means permitting said second gas stream to enter said first and second cavities when the pressure in said first cavity is greater than the pressure in said second cavity by an amount slightly greater than said predetermined initial pressure of said container.

20. An inflation system according to claim 19, further comprising third and fourth pressure relief means in air flow communication with said third gas stream, said pressure relief means operable to interrupt the flow of gas into said second regulator means if the pressure of said third gas stream is in excess of a predetermined level.

* * * * *